United States Patent [19]

Arkinstall

[11] Patent Number: 5,287,852
[45] Date of Patent: Feb. 22, 1994

[54] APPARATUS AND METHOD FOR MAINTAINING A TRACHEAL STOMA

[75] Inventor: William W. Arkinstall, Kelowna, Canada

[73] Assignee: Direct Trends International Ltd., Kelowna, Canada

[21] Appl. No.: 4,065

[22] Filed: Jan. 13, 1993

[51] Int. Cl.$^5$ ............................................. A61M 16/00
[52] U.S. Cl. ...................... 128/207.14; 128/DIG. 26; 128/200.24; 604/283; 604/80; 604/258; 604/905; 285/162; 411/19; 16/2
[58] Field of Search .................. 138/92; 285/158, 162; 52/221; 411/19, 360; 174/65 R, 65 SS, 65 G; 16/2; 604/283, 80, 258, 905; 128/DIG. 26, 207.14, 200.24

[56] References Cited

U.S. PATENT DOCUMENTS

| | | | |
|---|---|---|---|
| 4,246,897 | 1/1981 | Muto | 128/207.15 |
| 4,459,984 | 7/1984 | Liegner | 128/207.15 |
| 4,688,568 | 8/1987 | Frass et al. | 128/207.15 |
| 4,817,598 | 4/1989 | LaBombard | 128/207.14 |
| 4,919,127 | 4/1990 | Pell | 128/207.14 |
| 4,960,122 | 10/1990 | Mizus | 128/207.14 |
| 5,042,475 | 8/1991 | LaBombard | 128/207.14 |
| 5,052,386 | 10/1991 | Fischer, Jr. | 128/207.15 |
| 5,056,515 | 10/1991 | Abel | 128/207.15 |
| 5,058,580 | 10/1991 | Hazard | 128/207.15 |

FOREIGN PATENT DOCUMENTS

| | | |
|---|---|---|
| 1182022 | 2/1985 | Canada . |
| 2007080 | 8/1990 | Canada . |
| 2049155 | 2/1992 | Canada . |
| PCT/DK91/-00010 | 1/1991 | Denmark . |
| 0407663 | 6/1989 | European Pat. Off. . |
| 0371752 | 11/1989 | European Pat. Off. . |
| PCT/GB90/-00871 | 6/1990 | United Kingdom . |
| PCT/GB91/-00234 | 2/1991 | United Kingdom . |
| PCT/GB91/-00235 | 2/1991 | United Kingdom . |

Primary Examiner—Edgar S. Burr
Assistant Examiner—Eric P. Raciti
Attorney, Agent, or Firm—Bull, Housser & Tupper

[57] ABSTRACT

A releasably anchorable bushing conduit apparatus for providing access through a wall having a generally accessible side and a generally inaccessible side and an opening extending through the wall from the generally accessible side to the generally inaccessible side comprises a bushing conduit having first and second opposite end portions with first and second coterminous openings therein. The bushing conduit is insertable into the opening such that the first end portion protrudes from the wall on the inaccessible side and the second end portion protrudes from the wall on the accessible side. A retaining device external to the first and second coterminous openings retains the bushing conduit in place, yet presents no obstruction to the first and second coterminous openings. The retaining device includes an expandable and collapsible member secured to the first end portion and capable of expanding to interfere with the inaccessible side to prevent the first end portion from being withdrawn from the opening from the accessible side. The expandable and collapsible member is also capable of being collapsed to prevent interference of the member with the inaccessible side to permit the first end portion to be withdrawn from the opening. A device is provided on the bushing conduit for squeezing the wall between the expandable member and the second end portion to hold the bushing conduit securely in the wall opening.

24 Claims, 5 Drawing Sheets

APPARATUS AND METHOD FOR MAINTAINING A TRACHEAL STOMA

BACKGROUND OF THE INVENTION

The invention, in general, relates to an anchorable bushing for use in lining an opening to limit the size of the opening or to serve as a guide for items insertable into the opening. The device has a particular use as a temporary or permanently installed stoma lining for use in tracheostomy patients.

The problem of anchoring a device to an inaccessible side of a wall is ever present. Various devices have been devised to anchor various objects to a wall, such devices including barbed plugs, screws engaging an expanding leg member, rivets and the like. Few devices exist for anchoring a bushing to a wall, most relying on barbed projections for interfering with the walls defining the opening through which the bushing extends. Such devices are not readily removable from the opening and therefore have limited application. Preferably such anchorable bushings would be releasably anchorable in a wall opening to allow them to be removed from the opening. This would be advantageous in many applications including lining and maintaining a stoma formed during a tracheostomy.

Heretofore, at the time of tracheostomy, a cuffed endotracheal tube is inserted into the patient to permit controlled or assisted mechanical ventilation, removal of secretions and to provide access to the trachea. Currently available tracheostomy tubes provide an air tight seal in the trachea with inflatable cuffs which prevent air passage around the tracheostomy tube, either from the oral pharynx into the trachea and the tracheal bronchial tree distal to the tube, or retrograde from the tracheal bronchial airway past the cuff into the oral pharynx.

During weaning from assisted ventilation, patients are frequently initiated to the weaning process by disconnecting the patient from the ventilator to allow breathing through the open tracheostomy tube, either with air or with a supplemental oxygen supply. The tracheal tube and cuff creates a significant obstruction to the trachea, thereby interfering with the free flow of air in or out of the lungs both from the trachea, pharynx and mouth and from the tracheostomy tube. The tube and cuff markedly impedes any flow of air from the oral-pharynx in or out of the lungs.

When patients are able to be weaned from the assisted ventilation device, frequently the tracheostomy tube is changed to a non-cuffed tube to reduce the added obstruction of the tracheostomy tube and cuff and to provide a channel to clear secretions from the trachea and bronchial airways in the lungs. Non-cuffed tubes, have no air tight sealing cuffs and impose less obstruction to the trachea, but they still impede the free flow of air in and out of the lungs past the tracheostomy tube between the trachea and the oropharynx. To alleviate this impedance to air flow, tracheostomy tubes have been developed with a fenestration to provide communication between the oropharynx, through the fenestration into the trachea to allow for movement of air both around and through the tracheal tube fenestration and in and out of the lungs from the oropharynx.

Patients fitted with a non-cuffed tube may, however, not be fully recovered and therefore if the patient should again require assisted ventilation, the non-cuffed tube must be removed and a cuffed tube inserted to commence assisted ventilation. The aforementioned current cuffed tracheostomy tubes make it difficult to initiate spontaneous and normal breathing through the oropharynx because they are a mechanical obstruction in the trachea. Consequently, a tracheal tube change is frequently required to facilitate the weaning process. This can be uncomfortable to the patient and can subject the patient to the complications of frequent intubation and extubation.

Another problem with current ventilation methods is that during the weaning process, it is frequently necessary to maintain tracheal access to the lungs to assist in clearing secretions. In patients successfully weaned, the clearing of secretions is normally accomplished by coughing. An effective patient initiated cough requires a closed glottis to allow a pressure build-up, and a sudden decompression, when the glottis is opened to eject secretions. An open tracheostomy tube with an open channel from the trachea to the exterior of the body, precludes such a pressure build-up and therefore results in an ineffective, spontaneous cough.

Existing tracheostomy tubes must be inserted through an established tracheostomy. When the tube is removed from the patient, however, the stoma begins to heal. The healing process can take as little as 24 hours after which time reinsertion of the tracheostomy tube is impossible without a surgical revision to the stoma. Consequently further surgery is required in the event that further access to the trachea is necessary.

The above problems with assisted ventilation methods heretofore practiced arise because of the need to insert a plurality of different tubes into the ventilation opening at various stages of the weaning process, because of the need to close the ventilation opening to enable an effective cough once the patient has been successfully weaned and because of the rapid healing of a stoma. The insertion of the various tubes into the ventilation opening can be quite uncomfortable to the patient and closure of the opening is virtually the only way of enabling a patient to cause an effective spontaneous cough. With regard to healing of the stoma, it would be desirable to maintain the stoma until it is known for certain that it is no longer required.

One device which attempts to solve the above problems is the Olympic Trach-Button (trademark) which is a self retaining hollow cannula having an expansion lock comprised of a plurality of "petals" on a distal end thereof. The cannula is inserted into a tracheal stoma and a closure plug is inserted into the hollow cannula to expand the petals causing them to interfere with the anterior tracheal wall to prevent the cannula from being ejected. The closure plug or a ventilator adapter must always be inserted in the cannula in order to keep the petals expanded. Furthermore the cannula is of a fixed length and therefore spacers must be used to adapt it to fit the patient's stoma. Such spacers offer adjustment of the length of the cannula in discrete steps only and the spacers can irritate the exterior of the stoma resulting in discomfort to the patient. Cuffed or non-cuffed tracheostomy tubes or suction tubes may be inserted through the cannula, into the patient, to perform their respective functions.

The present invention addresses the problems with the Olympic Trach-Button and more generally addresses the problem of anchoring a bushing in a wall having only one accessible side. Cuffed, non-cuffed tracheostomy tubes or suction tubes may be inserted through the cannula, into the patient, to perform their respective functions.

SUMMARY OF THE INVENTION

In accordance with one aspect of the invention there is provided a releasably anchorable bushing conduit apparatus for providing access through a wall having a generally accessible side and a generally inaccessible side and an opening extending through the wall from the generally accessible side to the generally inaccessible side. The apparatus includes a bushing conduit having first and second opposite end portions with first and second coterminous openings therein. The bushing conduit is insertable into the opening in the wall such that the first end portion protrudes from the wall on the inaccessible side and the second end portion protrudes from the wall on the accessible side. A retaining device external to the first and second coterminous openings retains the bushing conduit in place, yet presents no obstruction to the first and second openings. The retaining device includes an expandable and collapsible member secured to the first end portion and capable of expanding to interfere with the inaccessible side to prevent the first end portion from being withdrawn from the opening from the accessible side. The expandable and collapsible member is also capable of being collapsed to permit the first end portion to be withdrawn from the opening when desired. A squeezing device is provided on the bushing conduit for squeezing the wall between the expandable member and the second end portion to hold the bushing conduit securely in the wall opening.

Preferably, the expandable member expands radially outwardly from the bushing conduit and includes a resilient membrane secured to the first end portion, the resilient membrane being inflatable with fluid such as air to form an annular ring about the first end portion.

Preferably, the apparatus includes a fluid conduit having a first end portion in communication with the expandable and collapsible member and a second end portion operable to receive fluid for inflating the expandable and collapsible member. Preferably, the fluid conduit has sufficient length to permit the second end portion to be located outwardly from the inaccessible side of the wall.

Preferably, the apparatus includes a removable plug operable to cover the second coterminous opening to prevent air from entering or exiting the conduit when access is not needed. When the apparatus is used on a tracheostomy patient, the use of the removable plug permits the patient to cough.

Preferably the second end portion is threaded, and a nut and washer are installed thereon to permit the wall to be squeezed between the expandable and collapsible member and the nut and washer. The use of the nut and washer enables the wall to be squeezed over a continuous range of forces which enables the apparatus to be installed securely, yet comfortably on a tracheostomy patient.

The apparatus may be used generally in any application which requires a bushing for lining purposes and access to an otherwise inaccessible side of a wall. This includes medical applications, generally wherever a stoma requires a lining. The apparatus has a particular use in an assisted ventilation opening where the wall is the patient's neck and the opening is the ventilation opening (stoma) extending through the neck, providing access to the trachea. The inaccessible side of the wall is therefore the anterior tracheal wall and the accessible side of the wall is the outer surface of the patient's neck. The bushing conduit is thus removably secured to the patient's neck. The unobstructed coterminous openings in the conduit permit the insertion of a cuffed endotracheal tube to provide an airtight seal in the trachea to allow for mechanical ventilation, allows easy access of a suction catheter to clear retained secretions, and enables a plug or other device to seal the ventilation opening to allow for near normal ventilation to and from the trachea via the oropharynx, without compromising the engagement of the retaining means with the anterior tracheal wall and without appreciably compromising air flow in the trachea.

In accordance with another aspect of the invention therefore, there is provided an apparatus and method for maintaining a tracheal stoma in a patient, the stoma extending through a wall defined by the anterior tracheal wall and the patient's neck. The apparatus is comprised of a cannula having first and second opposite end portions with first and second coterminous openings therein, the cannula being insertable into the stoma such that the first end portion protrudes into the trachea and the second end portion protrudes from the neck. Retaining means are provided for retaining the cannula in the stoma, the retaining means being external to the first and second coterminous openings to maintain the first and second coterminous openings unobstructed, the retaining means including an expandable and collapsible member secured to the first end portion and capable of expanding to interfere with the anterior tracheal wall to prevent the first end portion from being withdrawn from the stoma and capable of being collapsed to prevent interference of the member with the anterior tracheal wall to permit the first end portion to be withdrawn from the stoma. Squeezing means are also provided on the cannula for squeezing the wall, defined by the anterior tracheal wall and the neck, between the expandable member and the second end portion to hold the cannula securely in the stoma. The security of the cannula in the tracheal stoma is not dependent upon a closure element and is not compromised by intubation and extubation. Furthermore, the first and second openings are always maintained unobstructed which renders the tasks of intubation and extubation relatively easy. In addition, the squeezing means is continuously adjustable without requiring the removal of the cannula from the patient which allows the device to be comfortably installed and adjusted on the patient without irritating the exterior of the stoma.

BRIEF DESCRIPTION OF THE DRAWINGS

In drawings which illustrate embodiments of the invention.

DETAILED DESCRIPTION

Figure 1:
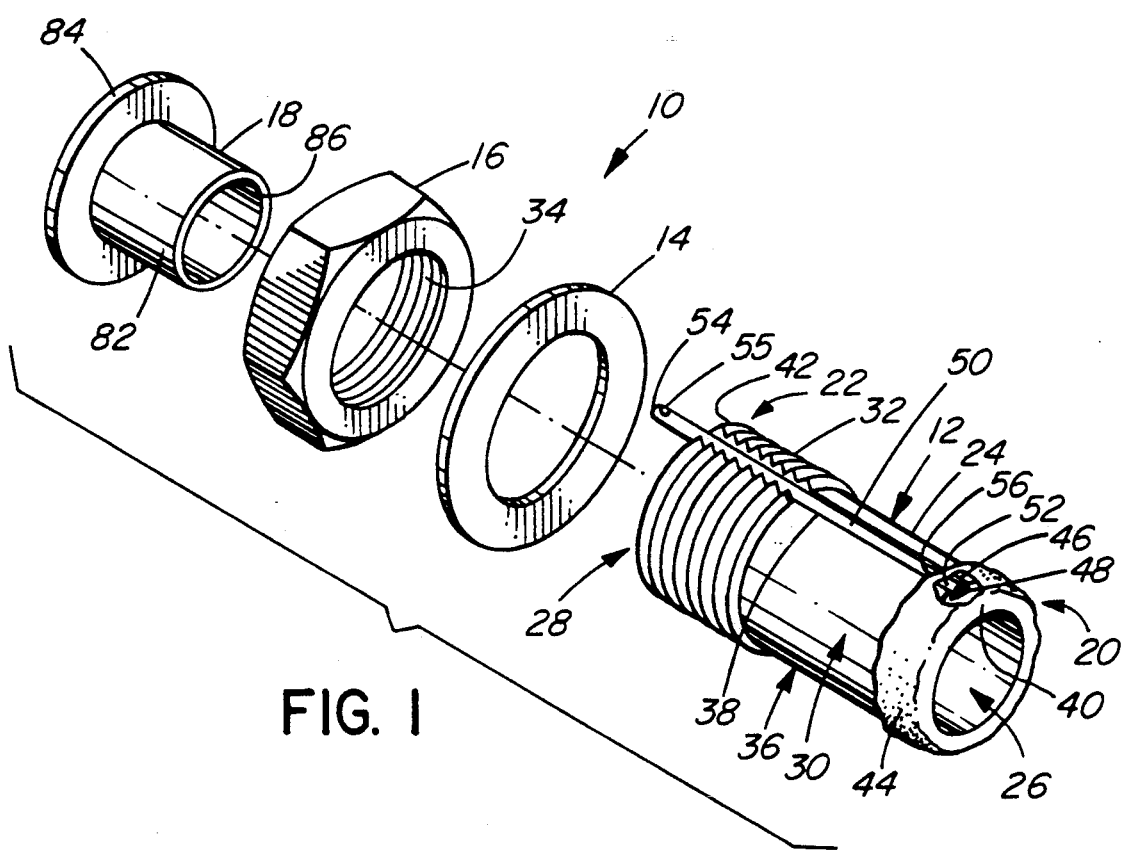
FIG. 1 is an exploded perspective view of a releasably anchorable bushing conduit according to a first embodiment of the invention.

Referring to FIG. 1, a releasably anchorable bushing conduit apparatus, for providing access through a wall having a generally accessible side and a generally inaccessible side and an opening extending through the wall from the generally accessible side to the generally inaccessible side, according to a first embodiment of the invention is shown generally at 10. The apparatus includes a bushing conduit 12, a washer 14, a nut 16, and a removable plug 18. The apparatus has a particular application in maintaining a tracheal stoma in a tracheostomy patient, in which application the bushing conduit is more properly referred to as a cannula. Thus the terms "bushing conduit" and "cannula" are deemed to be synonymous in this description.

The bushing conduit 12 is generally circular cylindrical in shape and has first and second opposite end portions shown generally at 20 and 22 respectively. Disposed between the end portions is an intermediate portion 24.

The first end portion 20 has a first end face 40 having a first opening 26 while the second end portion has a second end face 42 having a second opening 28. The first and second openings are coterminous such that a passageway is formed between the first and second openings 26 and 28.

The bushing conduit 12 has an outer wall 36 having a smooth cylindrical surface portion 30 which extends along the intermediate portion 24 and the first end portion 20. The second end portion 22 has a threaded portion 32 which extends there along toward the intermediate portion. The threaded portion 32 is operable to engage a set of corresponding complementary threads 34 on the nut 16.

A rectangular groove 38 is formed longitudinally in the outer wall 36 to extend between the first and second end portions 20 and 22. The groove 38 extends near to, but not entirely up to, the first end face 40 but does extend entirely through the second end face 42. The groove creates a discontinuity in the threaded portion 32.

A resilient balloon-like membrane 44 is secured to the first end portion 20 such that a portion 46 of the rectangular groove is covered thereby. The membrane is secured to the first end portion using a conventional methods normally used in connecting cuffs to endotracheal tubes. The resilient membrane is thus permanently connected to the first end portion of the bushing conduit.

The resilient membrane 44 is formed generally in the shape of an annular ring extending about the first end portion 20. But, care is taken to ensure that the membrane does not obstruct the first opening 28. An opening 48 is formed in the membrane to permit it to communicate with the rectangular groove 38.

A fluid conduit 50 operable to conduct air, is inserted into the groove 38 such that a first end portion 52 thereof is in communication with the membrane 44 and such that a second end portion 54 thereof extends outwardly past the second end portion 22 of the conduit. The second end portion 54 has a conventional spring loaded valve which selectively admits air into the fluid conduit and selectively prevents air from flowing therefrom. The flexible membrane 44 is attached to the fluid conduit 50 such that an air tight seal 56 is formed between the membrane 44 and fluid conduit 50. Air blown into the fluid conduit 50 is operable to inflate the membrane 44 to expand it generally radially outwardly from the bushing conduit to form a smooth-surfaced annular ring 68 extending about the first end portion 20, as seen best in FIG 2. Preferably, there is no expansion of the membrane beyond the first end portion 40. The membrane thus acts as an expandable and collapsible member secured to the first end portion and is capable of being expanded to interfere with the inaccessible side of a wall to prevent the first end portion from being withdrawn from an opening in the wall in which it is installed, and the expandable and collapsible member is capable of being collapsed to prevent interference of the member with the inaccessible side of the wall to permit the first end portion to be withdrawn from the opening.

The membrane and fluid conduit 50 together act as retaining means for retaining the bushing conduit in the opening, the retaining means being external to the first and second coterminous openings to maintain the first and second coterminous openings unobstructed.

Referring back to FIG. 1, the plug 18 has a shank portion 82 and a cap portion 84. The shank portion 82 has a slight taper and has a distal end portion 86 which is insertable into the second opening 28. Friction retains the plug in the opening.

OPERATION

The device shown in FIG. 1 may be used on virtually any wall having a generally accessible side and a generally inaccessible side and an opening extending through the wall from the generally accessible side to the generally inaccessible side. While the apparatus has general application, a specific application will be described below in which the device is used in a tracheal stoma.

Figure 2:
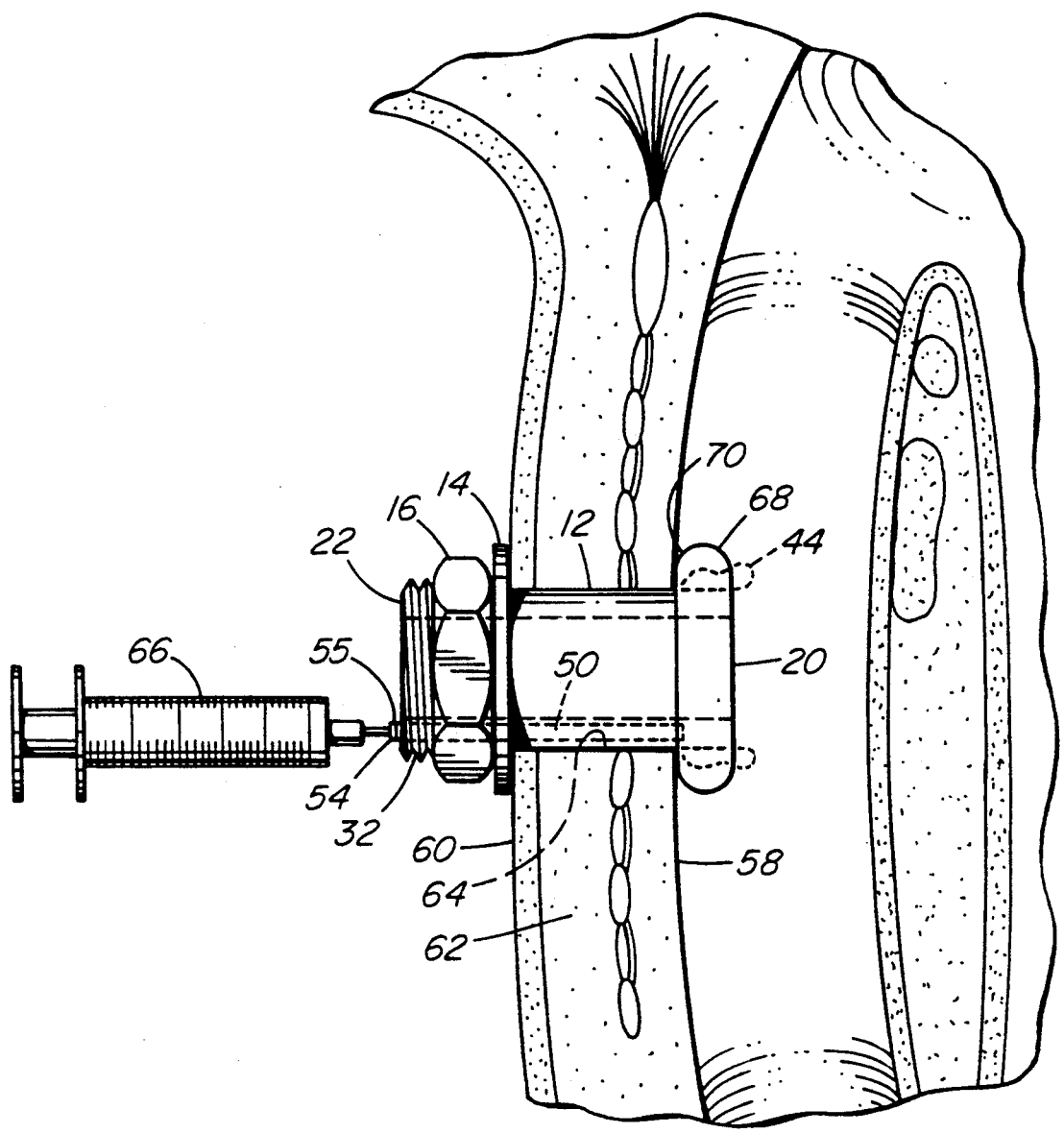
FIG. 2 is a cross-sectional view of the bushing conduit of FIG. 1 extending through a tracheal stoma.

Referring to FIG. 2, when the apparatus is used in a tracheal stoma, a wall is formed by that portion of a patient's neck bounded by the anterior tracheal wall 58 and the skin 60 generally seen on the outside of the patient's neck. In this embodiment, the wall is identified by numerical reference 62 and the tracheal stoma extending between the skin 60 and the anterior tracheal wall 58 is designated 64. The tracheal stoma, of course, corresponds to the opening recited in the claims.

To use the apparatus of FIG. 1 in a tracheal stoma such as shown in FIG. 2, the first end portion 20 is inserted into the tracheal stoma 64 such that the first end portion 20 protrudes from the anterior tracheal wall 58, into the trachea and such that the second end portion 22 protrudes from the skin 60 on the exterior side of the patient's neck. With the apparatus so installed, the membrane 44 will be in a flaccid state shown in broken outline.

A hypodermic syringe 66 or other suitable air blowing device is then inserted into the second end portion 54 of the fluid conduit 50 and is used to blow air through the fluid conduit 50 into the membrane 44. The air blown into the membrane expands the membrane to create an annular ring 68 about the first end portion 20. The annular ring has a smooth surface which acts as a first surface 70 for contacting the anterior tracheal wall 58 and interferes with the wall to prevent the first end portion from being withdrawn or expelled from the tracheal stoma 64. With the membrane 44 so inflated, the hypodermic syringe 66 may be withdrawn from the fluid conduit 50 whereupon the valve 55 closes and air prevented from escaping from the second end portion 54.

The washer 14 and nut 16 are then secured to the threaded portion 32. The washer has a second surface 15 disposed oppositely to the first surface 70 which enables the wall 62 to be squeezed between the first surface 70 on the annular ring 68 and the second surface 15 on the washer 14, to hold the cannula 12 securely in the tracheal stoma 64. The threaded portion 32, washer 14 and nut 16 act as squeezing means on the cannula for squeezing the wall, defined by the anterior tracheal wall and the neck, between the expandable member and the second end portion to hold the cannula securely in the stoma. The washer 14 acts as a squeezing member and has a continuous range of movement relative to the first end portion to permit the wall to be squeezed between the first and second surfaces at any desired force within a range of forces.

The apparatus is thus installed in the tracheal stoma 64 and provides a passageway from the outside of the patient's neck into the trachea. The annular ring 68 formed about the first end portion 20 presents only a minimal impedance to air flow in the trachea and therefore has a negligible effect upon the air flow therein.

Figure 3:
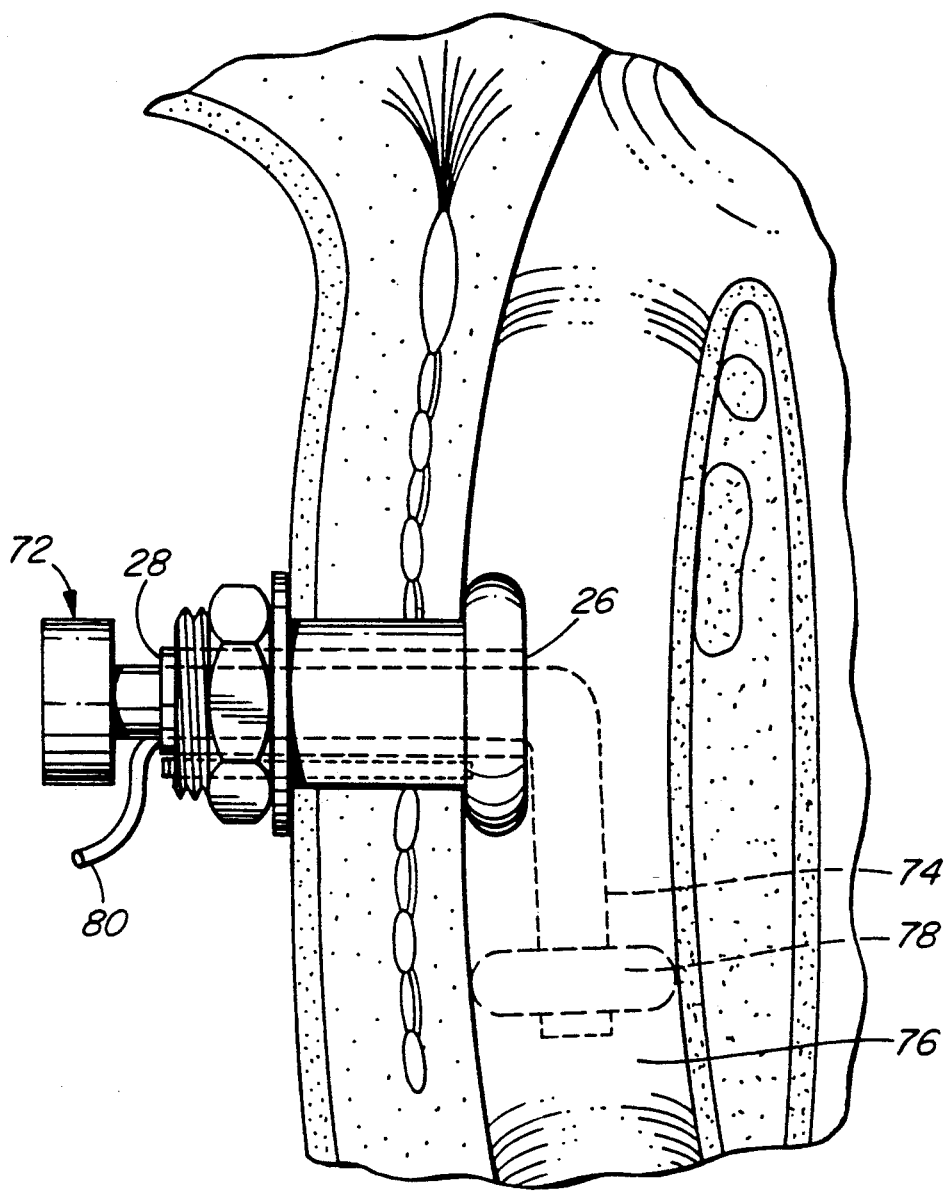
FIG. 3 is a cross-sectional view of the bushing conduit of FIG. 1 extending through a tracheal stoma with a cuffed endotracheal tube according to the prior art extending through the bushing conduit into the trachea.

Referring to FIG. 3, the apparatus permits the insertion of a conventional cuffed endotracheal tube shown generally at 72. The cuffed endotracheal tube 72 may be inserted through the second opening 28 to pass through the passageway in the cannula and out of the first opening 26 such that a cuffed portion 74 of the endotracheal tube extends downwards into the trachea 76. A cuff 78 on the endotracheal tube 72 may then be inflated using the conventional conduit 80 until the trachea is completely blocked by the cuff as is well known in the art. The cuffed endotracheal tube may then be connected to a ventilator to assist the patient in breathing. When the patient is to be weaned from the ventilator, the cuff 78 may be deflated and the cuffed endotracheal tube may be retracted from the second opening 28. The patient is then able to breath through the passageway between the first and second openings 26 and 28 in the cannula.

Figure 4:
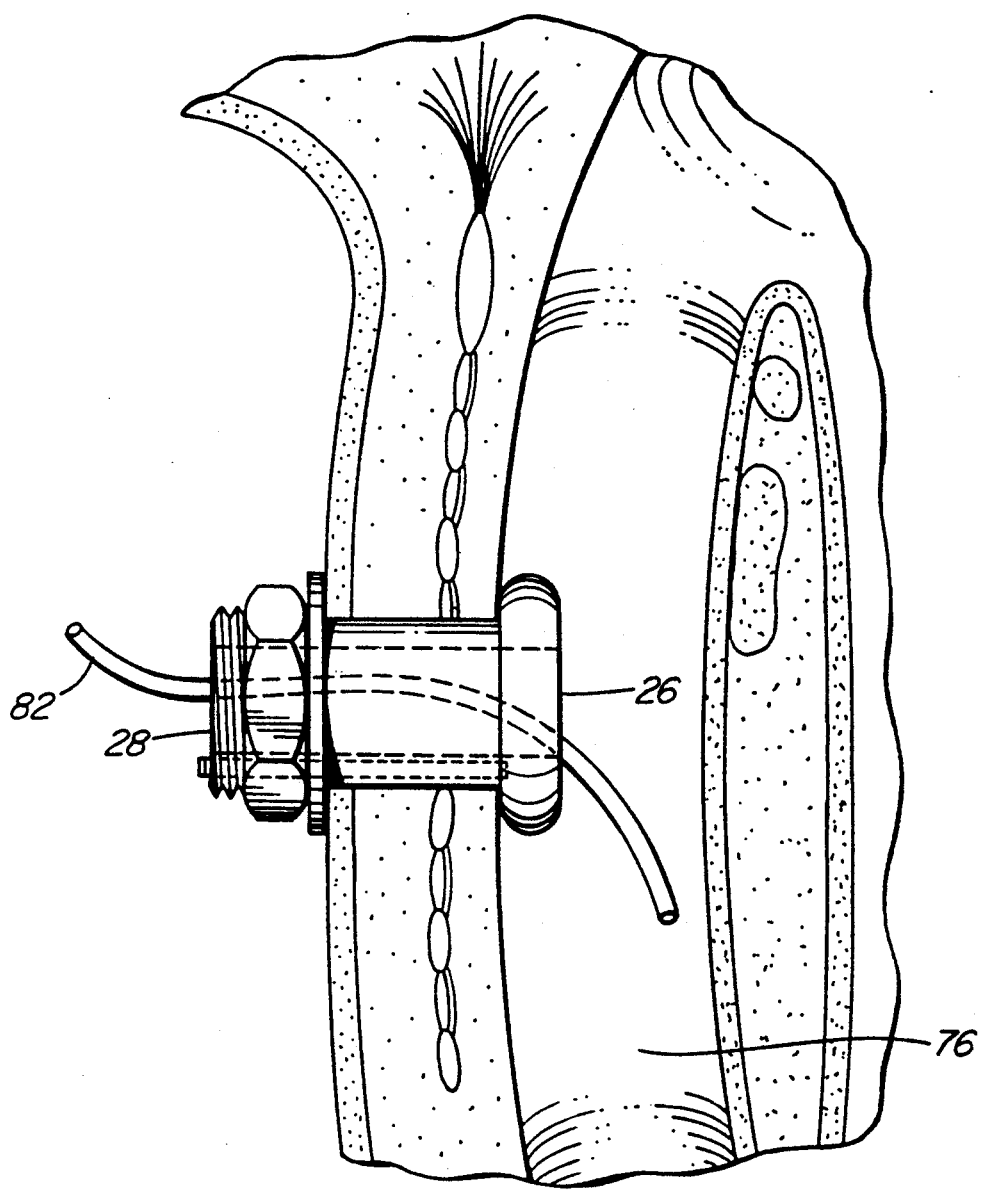
FIG. 4 is a cross-sectional view of the bushing conduit of FIG. 1 extending through a tracheal stoma with a suction catheter according to the prior art inserted through the bushing conduit into the trachea.

Referring to FIG. 4, should secretions accumulate in the trachea, a conventional catheter 90 may be inserted into the second opening 28 to extend through the passageway and out of the first opening 26 to extend down into the trachea 76. The catheter 90 may then be used to withdraw secretions from the trachea as is commonly known in the art.

Figure 5:
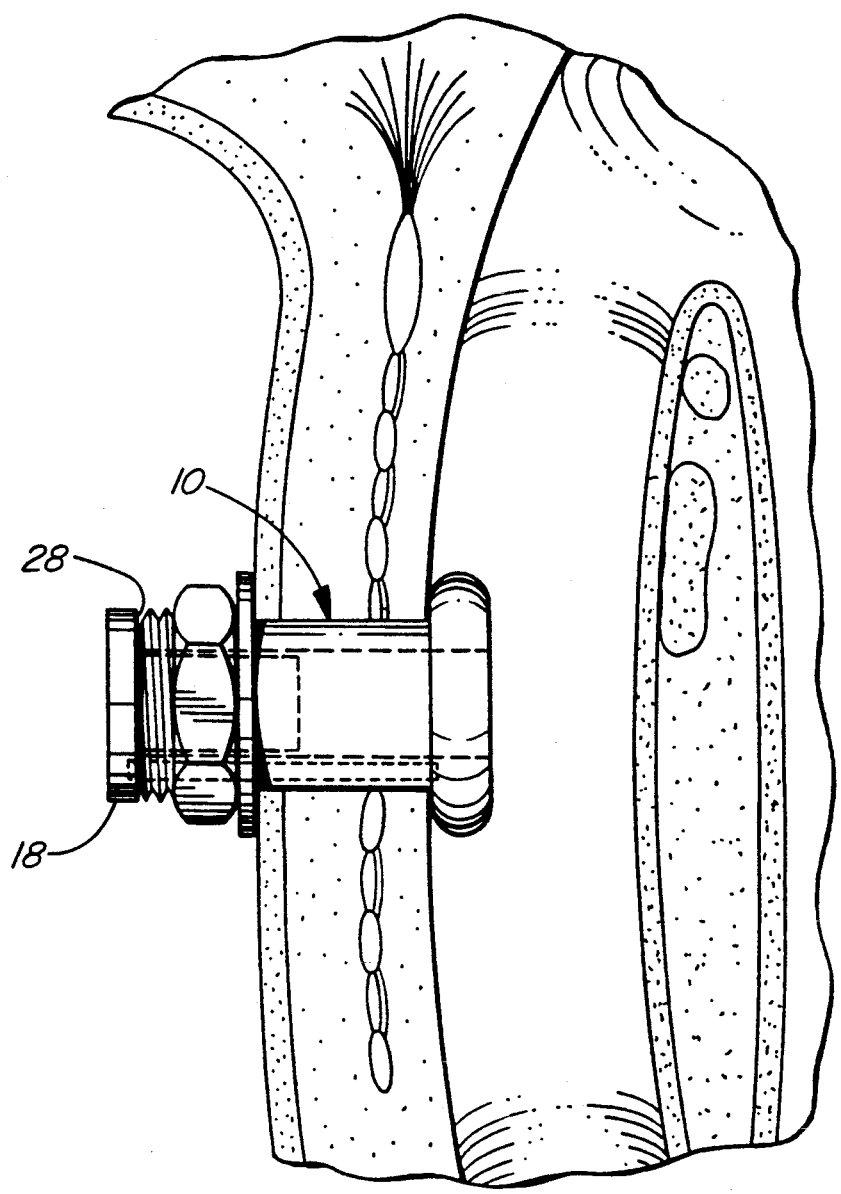
FIG. 5 is a cross-sectional view of the bushing conduit of FIG. 1 shown with a plug according to the invention shown installed therein.

Referring to FIG. 5, when the patient has been successfully weaned from the ventilator and is capable of breathing on his own, the plug 18 is inserted into the second opening 28 in order to seal the second opening and prevent air flow to and from the trachea through the cannula 12.

Referring back to FIG. 2, in the event that the patient no longer requires the cannula, the annular ring 68 can be deflated by withdrawing the air contained therein. The withdrawal of air can be accomplished by sucking the air out of the fluid conduit 50 and membrane 44, using the hypodermic syringe 66. The air is withdrawn until the membrane 44 is returned to the flaccid state, i.e. collapsed, whereupon the first end portion 20 may be withdrawn from the tracheal stoma 64. The membrane 44 thus acts as an expandable and collapsible member capable of being expanded to interfere with the inaccessible side of the wall to prevent the first end portion from being withdrawn and capable of being collapsed to prevent interference of the member with the inaccessible side to permit the first end portion to be withdrawn from the opening.

ALTERNATIVES

It will be appreciated that the bushing conduit may be straight or curved without affecting its function and advantages.

While specific embodiments of the invention have been described and illustrated, such embodiments should be considered illustrative of the invention only and not as limiting the invention as construed in accordance with the accompanying claims.

What is claimed is:

1. An apparatus for maintaining a tracheal stoma in a patient, the stoma extending through a wall defined by the anterior tracheal wall and the patient's neck, the apparatus comprising:
   a) a cannula having first and second opposite end portions with first and second coterminous openings therein, the cannula being insertable into the stoma such that the first end portion protrudes into the trachea and the second end portion protrudes from the neck;
   b) retaining means for retaining the cannula in the stoma, the retaining means being external to the first and second coterminous openings to maintain the first and second coterminous openings unobstructed, the retaining means including an expandable and collapsible member secured the first end portion and capable of expandable to interfere with the anterior tracheal wall to prevent the first end portion from being withdrawn from the stoma while presenting a negligible effect to airflow in the trachea and collapsible to prevent interference of the member with the anterior tracheal wall to permit the first end portion to be withdrawn from the stoma; and
   c) squeezing means on the cannula for squeezing the wall, defined by the anterior tracheal wall and the neck, between the expandable member and the second end portion to hold the cannula securely in the stoma.

2. An apparatus as claimed in claim 1 wherein the retaining means is permanently connected to the cannula.

3. An apparatus as claimed in claim 1 wherein the expandable member expands generally radially outwardly from the cannula.

4. An apparatus as claimed in claim 1 wherein the expandable and collapsible member has a relatively smooth surface for engaging the anterior tracheal wall without damage thereto.

5. An apparatus as claimed in claim 1 wherein the expandable and collapsible member includes a resilient membrane secured to the first end portion, the resilient membrane being inflatable with fluid.

6. An apparatus as claimed in claim 5 wherein the membrane forms an annular ring about the first end portion upon inflation.

7. An apparatus as claimed in claim 5 further including a fluid conduit having a first end portion in communication with the expandable and collapsible member and a second end portion operable to receive fluid for inflating the expandable and collapsible member.

8. An apparatus as claimed in claim 7 wherein the cannula has an outer surface, the outer surface having a groove formed longitudinally therein, the groove extending between the first and second end portions, the fluid conduit being located in the groove.

9. An apparatus as claimed in claim 1 wherein the expandable and collapsible member has a first surface for contacting the anterior tracheal wall.

10. An apparatus as claimed in claim 9 wherein the squeezing means includes a squeezing member having a second surface disposed oppositely to the first surface, the wall defined by the anterior tracheal wall and the outer surface of the neck being squeezed between the first and second surfaces.

11. An apparatus as claimed in claim 10 wherein the second surface of the squeezing member has a continuous range of movement relative to the first end portion to permit the wall to be squeezed between the first and second surfaces at any desired force within a range of forces.

12. An apparatus as claimed in claim 11 wherein the second end portion has a threaded portion, the squeezing means includes a nut engageable with the threaded end portion and wherein the squeezing member includes a washer urged toward the accessible side of the wall by the nut.

13. An apparatus as claimed in claim 1 further including a removable plug operable to cover the second coterminous opening to prevent air from entering or escaping from the cannula.

14. A method of maintaining a tracheal stoma in a patient, the stoma extending through a wall defined by the anterior tracheal wall and the patient's neck, the method comprising the steps of:
   a) inserting a first end portion of a cannula into a tracheal stoma such that the first end portion protrudes into the trachea and such that a second end portion of the conduit protrudes from the neck of the patient;
   b) expanding an expandable and collapsible member secured to the first end portion, while maintaining first and second coterminous openings of the cannula unobstructed such that said expandable member interferes with the anterior tracheal wall to prevent the first end portion from being withdrawn from the tracheal stoma from the neck, while presenting a negligible effect to airflow in the trachea; and
   c) squeezing the wall defined by the anterior tracheal wall and the neck, between the expandable member and the second end portion to hold the cannula securely in the tracheal stoma.

15. A method as claimed in claim 14 further including the step of expanding the expandable and collapsible member radially outwardly from the cannula.

16. A method as claimed in claim 14 further including the step of engaging the anterior tracheal wall with a relatively smooth surface to prevent damage thereto.

17. A method as claimed in claim 14 further including the step of inflating the expandable and collapsible member with fluid.

18. A method as claimed in claim 17 further including the step of forcing fluid into an end portion of a fluid conduit in communication with the expandable and collapsible member to inflate the expandable and collapsible member.

19. A method as claimed in claim 17 further including the step of inflating the expandable and collapsible member to form an annular ring about the first end portion.

20. A method as claimed in claim 14 further including the steps of contacting the anterior tracheal wall with a first surface on the expandable and collapsible member and squeezing the wall defined by the anterior tracheal wall and the patient's neck between the first surface and a second surface disposed oppositely to the first surface.

21. A method as claimed in claim 20 further including the step of urging a washer on which the second surface is disposed, toward the first surface.

22. A method as claimed in claim 14 further including the step of covering the second coterminous opening to prevent air from entering the cannula.

23. A method as claimed in claim 14 further including the step of collapsing the expandable and collapsible member to permit the first end portion to be withdrawn from the tracheal stoma.

24. A method as claimed in claim 23 further including the step of withdrawing the cannula from the tracheal stoma.

* * * * *